United States Patent
Gentempo et al.

(10) Patent No.: US 7,115,098 B2
(45) Date of Patent: Oct. 3, 2006

(54) ADJUSTABLE THERMAL SCANNING SYSTEM AND METHOD

(76) Inventors: Patrick Gentempo, 2 Augusta Ct., Tuxedo Park, NY (US) 10987; Lee Brody, 120 Pearson Rd., Somerville, MA (US) 02144

( * ) Notice: Subject to any disclaimer, the term of this patent is extended or adjusted under 35 U.S.C. 154(b) by 0 days.

(21) Appl. No.: 10/173,336

(22) Filed: Jun. 14, 2002

(65) Prior Publication Data
US 2002/0151817 A1    Oct. 17, 2002

Related U.S. Application Data

(63) Continuation of application No. 09/661,712, filed on Sep. 14, 2000, now Pat. No. 6,440,084.

(51) Int. Cl.
*A61B 5/00*    (2006.01)

(52) U.S. Cl. .................................................. 600/549

(58) Field of Classification Search ............ 600/549, 600/438, 474, 594
See application file for complete search history.

(56) References Cited

U.S. PATENT DOCUMENTS

| | | | |
|---|---|---|---|
| 1,552,284 A | | 9/1925 | Evins |
| 1,610,271 A | * | 12/1926 | Evins .......................... 136/224 |
| 2,297,868 A | * | 10/1942 | Bergeron ..................... 374/114 |
| 2,546,276 A | * | 3/1951 | Redding ...................... 600/549 |
| 3,830,224 A | * | 8/1974 | Vanzetti et al. ............. 600/549 |
| 3,830,970 A | | 8/1974 | Hurley et al. |
| 3,868,508 A | | 2/1975 | Lloyd |
| 3,970,074 A | * | 7/1976 | Mogos et al. ................ 600/549 |
| 4,010,367 A | | 3/1977 | Suzuki |
| 4,043,324 A | | 8/1977 | Shaw, IV |
| 4,055,166 A | * | 10/1977 | Simpson et al. ............. 600/549 |
| 4,186,748 A | | 2/1980 | Schlager |
| 4,218,707 A | | 8/1980 | Reed et al. |
| 4,347,854 A | * | 9/1982 | Gosline et al. .............. 600/549 |
| 4,366,381 A | | 12/1982 | Fischer et al. |
| 4,379,461 A | | 4/1983 | Nilsson et al. |
| 4,428,382 A | | 1/1984 | Walsall et al. |
| 4,445,516 A | | 5/1984 | Wollnik et al. |
| 4,461,301 A | | 7/1984 | Ochs |
| 4,479,498 A | | 10/1984 | Toftness |

(Continued)

OTHER PUBLICATIONS

Operation Manual, TyTron C-3000, Titronics Research & Development Company.
Brochure for "Subluxation™ Station", Chiropractic Leadership Alliance, 2000.
Brochure for "The Insight 7000 Subluxation Station™". Chiropractic Leadership Alliance.

*Primary Examiner*—Max F. Hindenburg
*Assistant Examiner*—Jonthan Foreman
(74) *Attorney, Agent, or Firm*—Knobbe, Martens, Olson & Bear LLP

(57) ABSTRACT

A thermal scanning system and method. The thermal scanning system comprises a handheld thermal scanning device with wheels and three infrared sensors that are spaced to scan skin temperature on opposite sides of patient spinal columns of different sizes. Two out of the three sensors are selected for a particular patient, and the wheels are adjustable to accommodate the two selected sensors. The handheld device further calculates the distance traveled by the wheels by measuring the rotation of the wheels. The device has a trigger that allows a user to annotate the location of various anatomical landmarks, such as particular regions of a patient's spinal column. The device is adapted to take discrete temperature readings or rolling temperature readings. The thermal scanning system provides graphical displays and data analysis of the temperature readings from the sensors.

17 Claims, 13 Drawing Sheets

U.S. PATENT DOCUMENTS

| | | |
|---|---|---|
| 4,849,885 A | 7/1989 | Stillwagon et al. |
| 5,050,612 A * | 9/1991 | Matsumura ................. 600/549 |
| 5,060,657 A | 10/1991 | Teague |
| 5,353,793 A * | 10/1994 | Bornn ........................ 600/386 |
| 6,398,740 B1 * | 6/2002 | Lavery et al. .............. 600/549 |
| 6,595,934 B1 * | 7/2003 | Hissong et al. ................ 601/3 |

* cited by examiner

Segmented Thermal Narrative View

ADJUSTABLE THERMAL SCANNING SYSTEM AND METHOD

RELATED CASE

This is a continuation application of U.S. patent application Ser. No. 09/661,712, filed Sep. 14, 2000 now U.S. Pat. No. 6,440,084, in the names of Patrick Gentempo and Lee Brody, entitled "Thermal Scanning System and Method," which has been allowed. U.S. patent application Ser. No. 09/661,712 is hereby incorporated herein by reference.

BACKGROUND OF THE INVENTION

1. Field of the Invention

The present invention relates to medical diagnostic equipment, and in particular to a thermal scanning system and method.

2. Description of the Related Art

Chiropractors and other health care professionals have previously used hand-held devices to measure skin temperature at a variety of locations along a patient's spinal column. The purpose of taking such measurements is to monitor skin temperatures surrounding the spine. Alterations in skin temperature readings may be indicative of abnormal autonomic nervous system activity, which in turn may indicate a spinal subluxation, or misalignment of adjacent vertebrae. Chiropractic care is directed toward locating and correcting subluxations by spinal adjustment. By creating a record of thermal readings paraspinally, i.e., along both left and right sides of a patient's spine, during the course of care, a chiropractor can quantitatively assess where subluxations exist, and how chiropractic care helps to alleviate them.

Prior thermal scanners have enabled users to take temperature readings in a variety of ways. Large, expensive, and complex thermography devices have been used to measure temperature at numerous locations across a patient's entire back, enabling the user to create a "thermograph" of the patient's entire spinal region. These systems have not been easily portable, nor practical for use in a chiropractor's office.

One prior art system suitable for chiropractors used a single infrared thermal sensor mounted in a hand held unit, sometimes called a "paddle." The drawback of that approach was that in order to take paraspinal readings, the user was required to take two passes along the spine, which is time consuming and inaccurate since the paraspinal readings are taken at different times.

A dual sensor thermal scanner was disclosed in U.S. Pat. No. 1,552,284 to Evins. However, that system required different paddles to be used in order to accommodate patients of different sizes, such as adults and small children.

Another prior art approach is reflected in U.S. Pat. No. 4,849,885 to Stillwagon, et al., which discloses using, for example, twelve spaced infrared sensors mounted on a single hand-held unit which is rolled along the patient's spine. By allowing the sensors to take continuous readings as the paddle is rolled, a continuous line graph of bilateral temperatures along the spine could be generated quickly. However, that system was complex since it required that the data generated by each of the multiple sensors be processed into a data matrix. Further, this system required the user to move the paddle at a uniform rate along the user's spine in order to properly correlate the temperature reading with the location along the patient's spine from which the reading was taken.

Smaller, simpler devices using only two infrared sensors mounted on a hand-held paddle have also been used in the chiropractic field. One such system has been marketed by Titronics Research & Development Company of Oxford, Iowa as the "TyTron C-3000." This system also used the continuous "rolling" technique. One drawback, however, was that since the infrared sensors were spaced apart a fixed distance, in order to take readings from different sized patients, the scanner had to be used in a different mode requiring multiple passes along the spine. In particular, a first pass was needed to take readings from one thermal sensor on one side of the spine, and a second pass was required to take readings from the other side of the spine.

A prior infrared sensor device was also marketed by EMG Consultants, Inc. of Maywood, N.J. as the "Insight 7000 Thermal Scanner." This system utilized two separate hand-held paddles, each incorporating a single infrared sensor. Thus, left and right side paraspinal readings could be taken simultaneously from patients of different sizes. One drawback of that system, however, was that the user was required to use both hands to hold the paddles. Also, that system did not permit continuous, or "rolling" scans, but rather was limited to a series of static or discrete readings at selected locations. However, it did permit scanning at discrete locations off the paraspinal axis by holding the two paddles at different angles. This enabled readings at the anterior fossia of the ears, referred to as the "atlas," or the vertebra marked C1, which was not possible with prior "rolling" scanners.

While the foregoing summary identifies some of the drawbacks of the prior art, it is not an exhaustive listing of all the features of the prior art, nor of all the differences between the present invention and the prior art.

Thus, a need exists for a simple, easy to use, hand-held thermal scanning device which is adaptable for use with patients of various sizes. Moreover, a need exists for a system which accurately correlates temperature readings with the location along the patient's spine from which the reading is taken.

SUMMARY OF THE INVENTION

The present invention relates to an improved thermal scanning system, device and method. The present invention has several advantages and features. First, one embodiment of the thermal scanning device is advantageously adaptable to scan patients of various anatomical sizes, such as an infant, a child or an adult patient. The adaptability of the thermal scanning device eliminates the cost of purchasing and maintaining three separate instruments, one adapted for an infant, another adapted for a child and another adapted for an adult.

Second, one embodiment of the thermal scanning device provides more accurate mapping of thermal data by: (1) calculating the distance traveled by the device; and (2) allowing a user to annotate the location of various anatomical landmarks, such as particular regions of a patient's spinal column. The distance-calculating ability of the present invention improves the accuracy of temperature mappings for each section of the spine. In addition, the ability to calculate the distance traveled and to annotate the location of various anatomical landmarks eliminates the need to roll a thermal scanning device up a patient's spine at a uniform rate. In other words, the preferred embodiment of the thermal scanning device does not record time-dependent data. Thus, the user does not have to start the scan over if the user advances the thermal scanning device at an irregular pace along a patient's back. One disadvantage of repeating the thermal scan is that the patient's skin temperature changes after the initial scan, in part due to contact between the scanner and the skin surrounding the spine. The preferred thermal scanning device minimizes repeat scans, a drawback commonly associated with a time-dependent thermal scanning device.

Third, an embodiment of the thermal scanning device allows the user to alternate between static temperature readings at discrete locations, and continuous rolling temperature scanning. A single system capable of operating in both "rolling" and "static" modes has not been previously available.

Fourth, the thermal scanning system provides graphical readouts and data analysis of instantaneous bilateral differential temperature. The rolling operation of the thermal scanning device allows the user to scan multiple points on the skin consecutively and observe localized changes in skin temperature.

One aspect of the invention relates to a thermal scanning system adapted to scan skin temperature on opposite sides of a patient's spinal column for patients of different sizes. The thermal scanning system comprises a handheld body, a plurality of temperature sensors comprising a first sensor, a second sensor and a third sensor. The sensors are coupled to the body and arranged in a pattern. The first and second sensors are spaced and adapted to scan skin temperature on opposite sides of a patient's spinal column for patients of a first size range. The second and third sensors are spaced and adapted to scan skin temperature on opposite sides of a patient's spinal column for patients of a second size range. The first and third sensors are spaced and adapted to scan skin temperature on opposite sides of a patient's spinal column for patients of a third size range.

Another aspect of the invention relates to a thermal scanning system adapted to scan skin temperature on opposite sides of a patient's spinal column as a user advances a handheld scanning device along the patient's spinal column. The thermal scanning system comprises a handheld body, a first and a second temperature sensor and a detector. The first temperature sensor scans a left portion of the patient's spinal column. The second temperature sensor scans a right portion of the patient's spinal column. The detector detects a distance traveled by the handheld body along the patient's spinal column.

Another aspect of the invention relates to a method of scanning skin temperature on opposite sides of a patient's spinal column for patients of different sizes. The method comprises selecting two out of three thermal sensors which are arranged in a pattern, placing the two sensors on opposite sides of a patient's spinal column, and scanning skin temperature with the two sensors on opposite sides of the patient's spinal column.

Another aspect of the invention relates to a method of scanning skin temperature on opposite sides of a patient's spinal column. The method comprises advancing a handheld scanning device along the patient's spinal column, scanning a left portion of the patient's spinal column with a first temperature sensor, scanning a right portion of the patient's spinal column with a second temperature sensor, and detecting a distance traveled by the handheld scanning device along the patient's spinal column.

BRIEF DESCRIPTION OF THE DRAWINGS

FIG. 7 illustrates one embodiment of a table display for a rolling thermal scan.

FIG. 12 illustrates one embodiment of a table display for a segmental thermal scan.

FIG. 13 illustrates one embodiment of a narrative display for a segmental thermal scan.

DETAILED DESCRIPTION

The present invention relates to a thermal scanning system, device and method. In one embodiment of the thermal scanning system, there are two types of scanning and assessment methods: (1) rolling thermal scanning; and (2) segmental thermal scanning.

Figure 1:
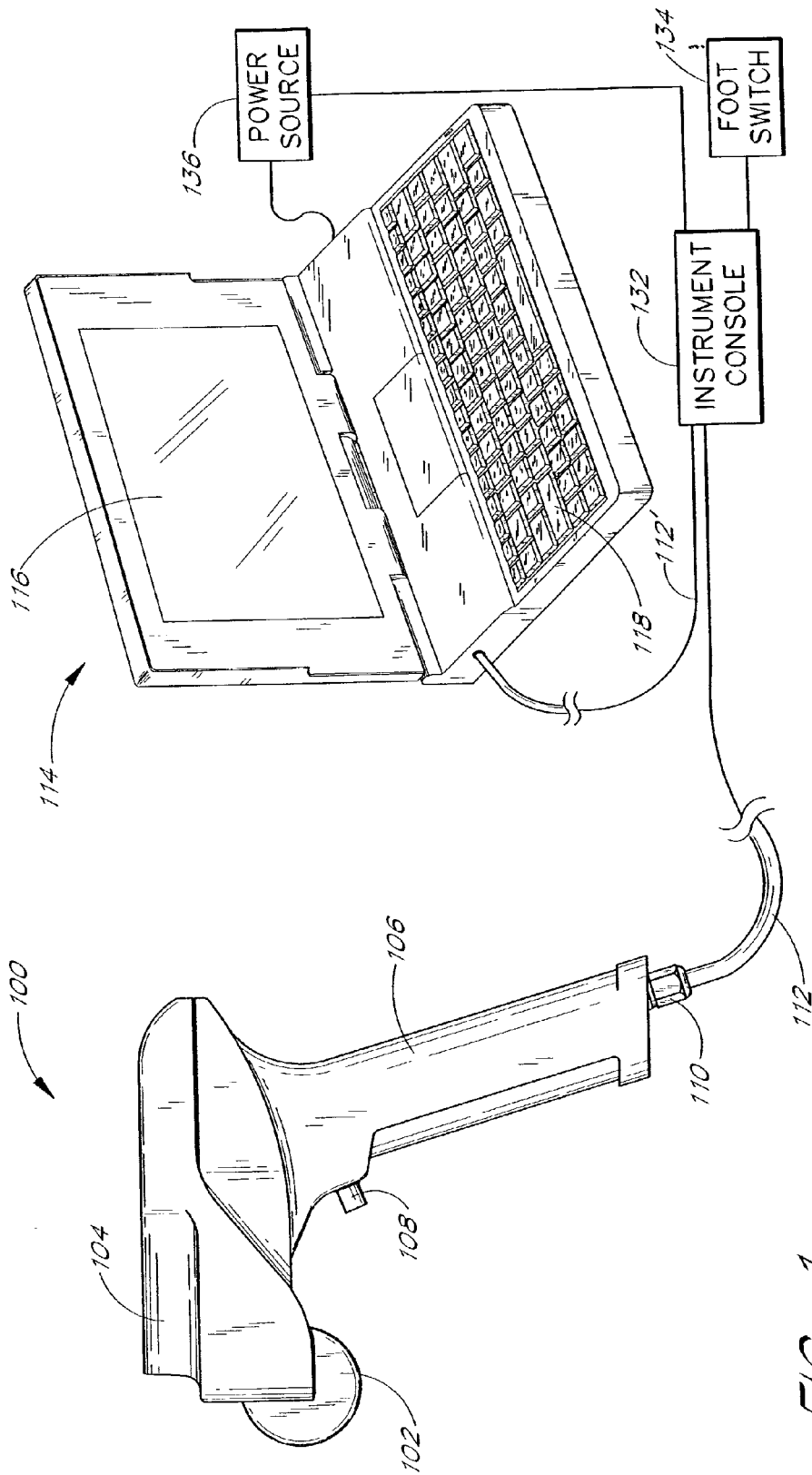
FIG. 1 illustrates one embodiment of a thermal scanning system.

FIG. 1 illustrates one embodiment of a thermal scanning system that comprises a handheld thermal scanning device or paddle 100, a computer 114, an instrument console 132 and a foot switch 134. The thermal scanning device 100 is coupled to the instrument console 132 via a cable 112. The instrument console 132 is coupled to the computer 114 via a cable 112'. Specifically, one end of the cable 112' is coupled to a PC RS232 connector of the instrument console 132 and the other end of the cable 112' is coupled to coupled to a 9-pin serial port, a 25-pin serial port or some other suitable port on the computer 114. The instrument console 132 is also coupled to a foot switch 143. Both the computer 114 and the instrument console 132 may be coupled to an external power source 136.

Figure 2:
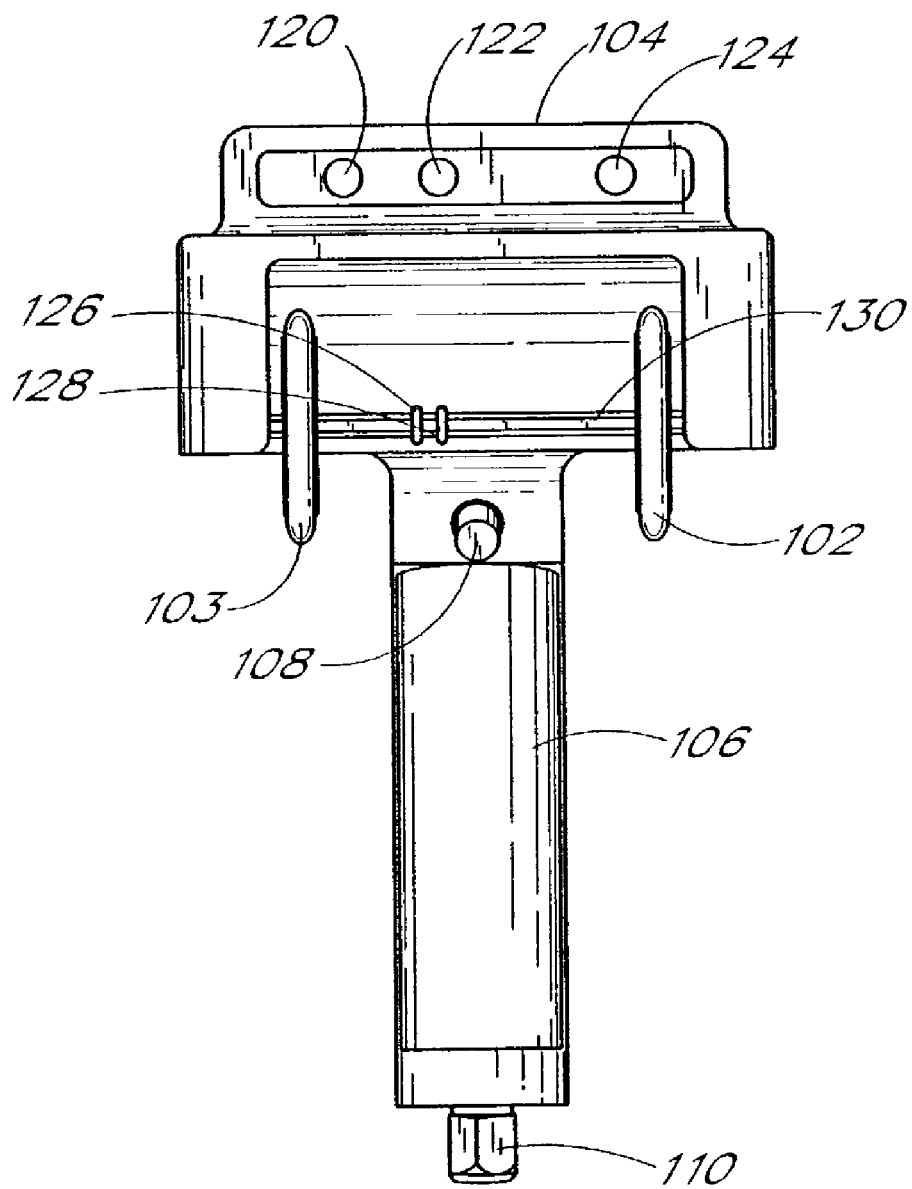
FIG. 2 is a frontal view of the hand-held thermal scanning device shown in FIG. 1.

As shown in FIGS. 1 and 2, the hand-held paddle 100 comprises a base 104, a first wheel 102, a second wheel 103, a handle 106, a trigger 108 and an adapter port 110. The computer 114 comprises a keyboard or other input device 118 and a display 116. In one embodiment, the computer 114 is a Pentium-based IBM PC-compatible computer, and preferably is a portable laptop. In one embodiment, the instrument console 132 is a microprocessor-controlled device that runs a control program downloaded initially from the computer 114.

FIG. 2 is a frontal view of the thermal scanning device 100 of FIG. 1. As shown in FIG. 2, the device 100 further comprises a first sensor 120, a second sensor 122, a third sensor 124, a first spacer 126, a second spacer 128 and a shaft 130. In one embodiment, the wheels 102, 103 are made of ABS plastic with a rubber O-ring surrounding the periphery of the wheel. In other embodiments, the device 100 may have one wheel or more than two wheels. In other embodiments, instead of wheels, the device 100 may have other means of keeping the sensors 120–124 above the patient's skin, such as a cushion of air like a hovercraft.

The base 104 includes an internal sensor, preferably a two-bit encoder with resolution of 0.2 inches, that senses the rotation of the shaft 130. The device 100, the instrument console 132 and/or the computer 114 may use the measured rotation of the shaft 130 and the known circumference of the wheels 102, 103 to calculate the distance traveled by the wheels 102, 103. In one embodiment, the shaft 130 is made of aluminum and has a polygonal cross-section which preferably is hexagonal. The spacers 126, 128 are preferably also formed from rubber O-rings which are sized to fit snugly over the shaft 130 so as to remain fixed along the shaft 130 during normal operation.

In one embodiment, the position of the wheels 102, 103 may be adjusted by the user by sliding the wheels 102, 103 axially along the shaft 130. The spacers 126, 128 may act as stops for the optimal locations of the wheels 102, 103 depending on which sensors 120–124 are being used. For example, if the second and third sensors 122, 124 are being used, the second wheel 103 may be positioned adjacent and to the left of the first spacer 126. The first wheel 102 may be positioned to the far right end of the shaft 130.

In one embodiment, the sensors 120–124 are 'non-contact' sensors that contain sensitive infrared cameras which detect the temperature of a target area, such as skin temperature, without touching the target area. The non-contact sensors 120–124 improve the reliability of temperature readings by minimizing the thermal energy transferred from the skin to the sensors 120–124 in contrast to sensors that are in direct contact with the skin. The sensors preferably are thermopiles having an optical system using a fresnel lens and an optical stop to produce a columnar beam of 0.25 inch diameter. The device also includes a thermistor (not shown), which determines the ambient temperature of the thermopile sensors. Alternatively, other types of sensors may be used, such as thermocouple devices.

Preferably, the sensors 120 and 124 are spaced 1.75 inches apart, center to center. Sensors 122 and 124 are likewise spaced 1.0 inches apart. Sensors 120 and 122 are thus spaced apart by 0.75 inches.

In general, a user rolls the thermal scanning device 100 with the wheels 102, 103 along a region of a patient's skin to be analyzed. The rolling operation of the device 100 allows the user to scan multiple points on the skin consecutively and observe localized changes in skin temperature in real-time, if desired, on the display 116 of the computer 114. The device 100 transmits sensor data to the instrument console 132, which transmits the data to the computer 114. The computer 114 stores and executes a Windows-based software program that analyzes, stores and displays the data. The use and operation of the device 100, the instrument console 132 and the computer 114 are described in further detail below.

Adaptable for Different Patients

The thermal scanning device 100 may be advantageously adapted to scan patients of various anatomical sizes, such as an infant, a child or an adult. In general, an infant's spinal column is smaller than a child's spinal column, and a child's spinal column is smaller than an adult's spinal column. The wheels 102, 103 and two of the three sensors are preferably spaced at equal distances from the central, vertical axis of the spine as the user advances the device 100 along a patient's back to detect the skin temperature. The user may advantageously use the position of the wheels 102, 103 as a visual guide to properly align the appropriate pair of sensors 120, 122, 124 at equal distances from either side of the spine. By centering the wheels on either side of the spine, the appropriate sensors will be properly centered as well.

For example, for an infant, the wheels 102, 103 may be adjusted to be aligned adjacent the first and second sensors 120, 122. Before scanning, the user positions the second wheel 103 to the far left end of the shaft 130 and positions the first wheel 102 adjacent and to the right of the second spacer 128. The wheels 102, 103 are positioned such that the wheels 102, 103 and first and second sensors 120, 122 are spaced at equal distances from the central, vertical axis of the spine of an infant. Before initiating the scan the user selects an "infant mode" in the software so that only the data gathered by the sensors 120 and 122 is stored by the computer 114 and processed for appropriate displays, as discussed below.

For a child, the wheels are adjusted to center the second sensor 122 and the third sensor 124 about the child's spine. Before scanning, the user positions the second wheel 103 adjacent and to the left of the first spacer 126 and positions the first wheel 102 to the far right end of the shaft 130. For an adult, before scanning, the user positions the second wheel 103 to the far left of the shaft 130 and positions the first wheel 102 to the far right end of the shaft 130, as shown in FIG. 2. In each case, the user selects the appropriate mode in the software so that the readings from the two sensors which are equally spaced paraspinally are recorded.

While these different settings are preferably used for infant, child and adult patients, the different settings can be used to accommodate different sized patients regardless of their age.

In an alternate embodiment (not shown), a pair of sensors are attached to the paddle so that the sensors are movable relative to one another. In that embodiment, different patient sizes would be accommodated by moving the sensors farther apart for larger patients, and closer together for smaller patients. In yet another alternate embodiment (not shown), waveguides may be attached to the sensors to direct the infrared radiation to the sensors. The waveguides may be adjustable to accommodate various size patients.

Roll Scanning

The thermal scanning device 100 allows both static/discrete temperature readings and roll temperature scanning. The thermal scanning device 100 also provides more accurate mapping of thermal data by allowing the user to annotate the location of various anatomical landmarks, such as the beginning and the end of each region of a patient's spinal column, during a rolling scan.

Figure 3:
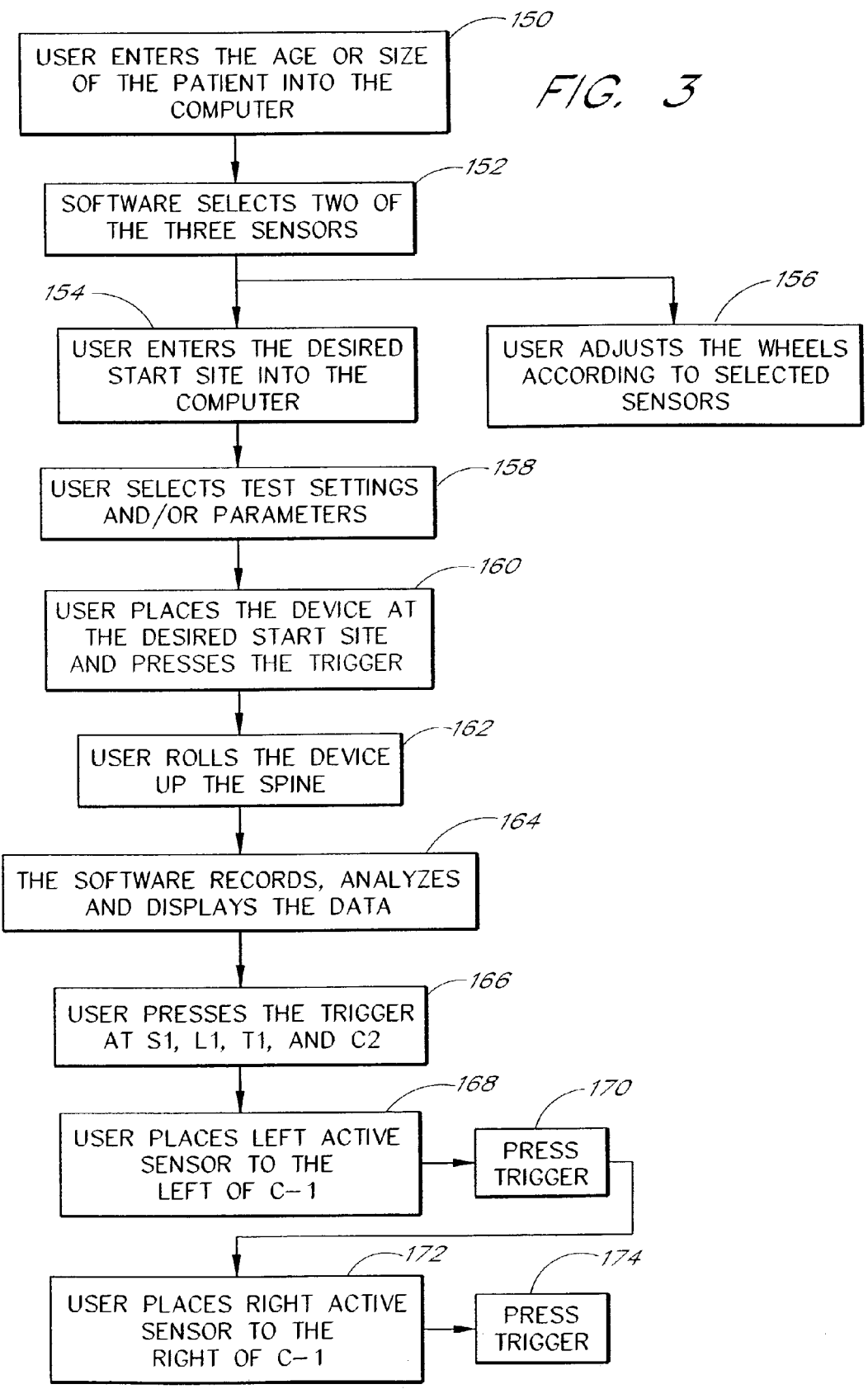
FIG. 3 illustrates one embodiment of the steps used in a rolling thermal scan method.

FIG. 3 illustrates one embodiment of a rolling thermal scan method. In a process block 150, the software prompts the user to enter the age or age group (infant, child, adult) of the patient into the computer 114 or the instrument console 132. In another embodiment, the user enters a size of the patient, such as small, medium or large. After the user enters the age or size, the software determines which two sensors 120, 122, 124 to use in the scan in a block 152. In another embodiment, the user determines which two of the sensors 120, 122, 124 to use and manually sets the software to use the readings from the two sensors selected by the user.

In a step represented by block 156, the user adjusts the wheels 102, 103 according to the selected two sensors 120–124. In a step shown in block 154, the user enters a desired start site into the computer 114. In a step shown in block 158, the user may select various test settings and/or enter various parameters. For instance, in one embodiment, the user may instruct the software to display a warning flag and/or stop the scan if the user rolls the thermal scanning device 100 too quickly. If the user rolls the device 100 too quickly, the software notifies the user, and the user simply restarts the scan. In addition, the user may select a temperature range, such as 6 degrees Fahrenheit or 8 degrees Fahrenheit. The user may also enable or disable a sound feature. The sound feature informs the user when the system is ready to begin scanning and which parts of the spine the user is scanning or should be scanning.

Figure 4:
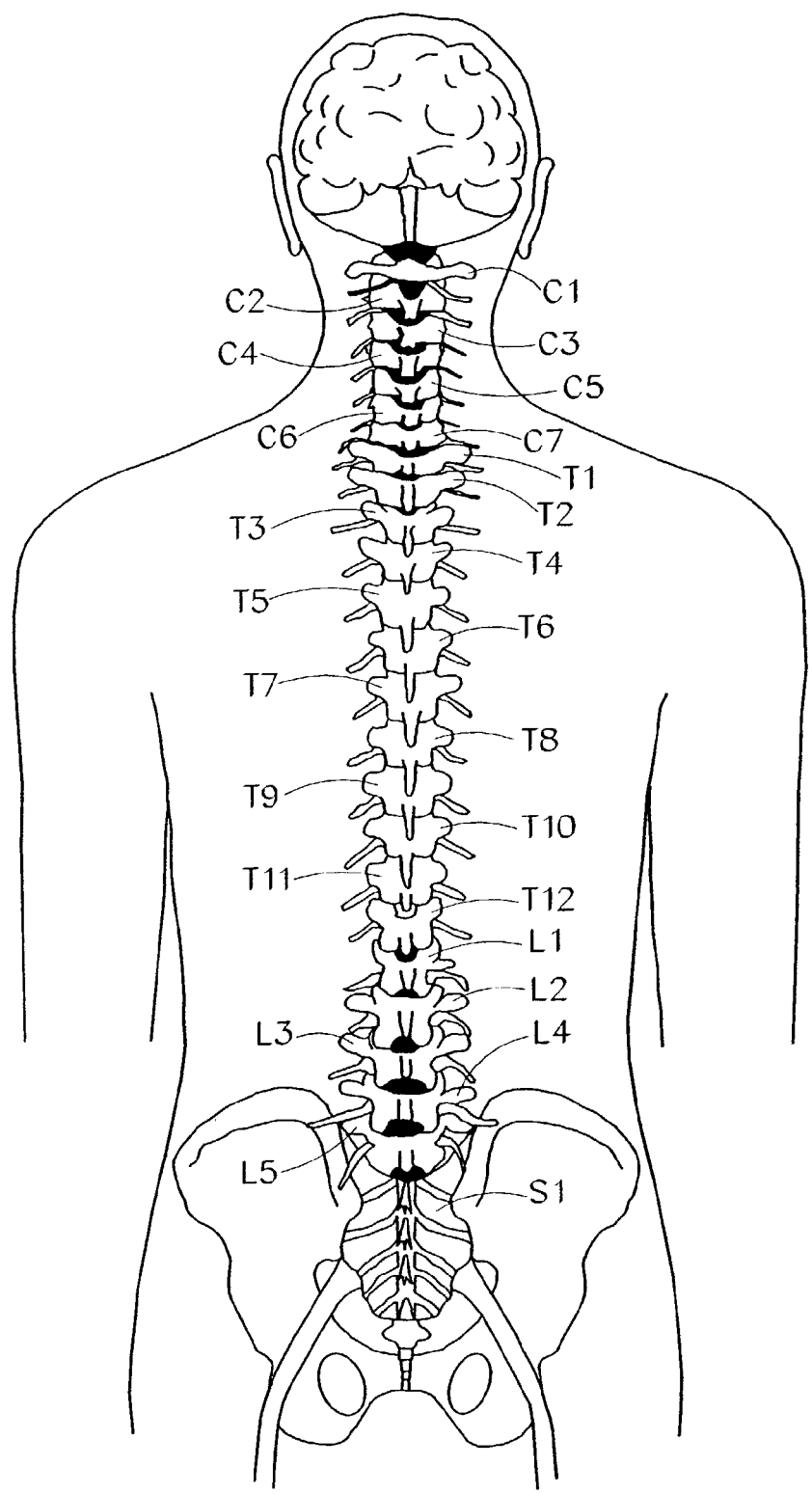
FIG. 4 illustrates a human spinal column.

In a step represented by block 160, the user places the device 100 at the desired start site, such as the base of a patient's spine, with the wheels 102, 103 touching the patient's skin and the sensors 120–124 pointed at two points at equal distance from the vertical, central axis of the spine. FIG. 4 illustrates an example of a human spinal column, and indicates the location of the first vertebrae in the sacral region, referred to as "S-1", which is a common starting point for such a scan. The user then presses the trigger 108 to indicate the start of the scan. In a block 162, the user rolls the device 100 up the spine to the patient's neck. The sensors 120–124 may take continuous thermal readings or incremental thermal readings.

In a block 164, the sensors 120–124 begin to transmit the thermal readings to the computer 114, and the software begins to collect, process and/or display the thermal readings for the two sensors that have been selected. In one embodiment, the device 100 and/or the instrument console 132 includes a sample-and-hold circuit which holds the value of one or more temperature readings by the sensors 120–124.

For example, if the device 100 is being used to scan an adult, the first and the third sensors 120, 124 transmit thermal readings to the computer 114. The sensor which has not been selected, the second sensor 122, continues to take readings but advantageously the software does not need to process any data from the second sensor 122.

In a block 166, the user presses the trigger again at the end of each spinal region (i.e., the beginning of each new region) to annotate the location of each region for further analysis by the software. As shown in FIG. 4, the spine comprises four regions starting at the bottom: the sacrum, the lumbar, the thoracic and the cervical. Each region comprises one or more vertebrae. For example, the cervical comprises seven vertebrae labeled as C-1, C-2, C-3, C-4, C-5, C-6 and C-7. Thus, the user presses the trigger 108 at approximate locations of S-1, L-1, T-1, and C-2.

In one embodiment, the device 100 also measures the rotation of the shaft 130, calculates the distance traveled by the wheels 102, 103 and transmits the calculated distance to the instrument console 132 and the computer 114. In another embodiment, the device 100 transmits the measured rotation of the shaft 130 to the instrument console 132, and the instrument console 132 and/or the computer 114 calculates the distance traveled by the wheels 102, 103.

Preferably, the software senses when the user advances the device 100 near the vertebra C-2. The software ends rolling scan mode and begins a discrete temperature read mode that allows a user to take discrete, off-axis temperature readings by pressing the trigger 108 each time the user desires a discrete temperature reading. Discrete temperature read mode is described in more detail below. In a block 168, the user places the left active sensor to the left of C-1, the top vertebra, and presses the trigger 108 in a block 170. In a block 172, the user places the right active sensor to the right of C-1 and presses the trigger 108 in a block 174.

Static/Discrete Temperature Readings

As described above, the device 100 may be used for discrete temperature readings at any one location, or at a group of locations along the spine. For example, the user may select a discrete or "segmental" temperature read option from the software and take a discrete temperature reading above the hair-line corresponding to a single vertebra in the upper cervical area. Alternatively, the user can select and scan a group of vertebra, such as all the vertebra in the lumbar region, or even the entire spine. The discrete or "segmental" mode differs from the "rolling" mode in that the user can select the precise number and location of sites to scan, and need not scan the entire spine. Moreover, in discrete mode the user can select sites off-axis from the spine, such as the anterior fossia behind the ear, or "atlas." The system is unique in that it permits the user to alternate between a rolling mode and a discrete or segmental mode.

During discrete mode, the user positions the device 100 at the location to be scanned, and presses the trigger. The device 100 is then moved to the next location at which a thermal reading is desired, and the user presses the trigger at that location.

Graphs and Displays

The software stored at the computer 114 provides various graphical display formats to display thermal patterns and symmetry or lack of symmetry. The software has the unique capability to correlate accurately the temperature measured with the location of individual vertebra on the patient's spine. The software contains normative data regarding the vertical length of each vertebrae for patients of different sizes, ages, or other unique characteristics which influence spinal anatomy. The software processes: (1) the normative data regarding typical positions of each vertebra; (2) the distance traveled by the wheels 102, 103; (3) the location of each place where the user pressed the trigger 108, indicating an anatomical landmark, preferably a transition to a different region; and (4) the scanned left and right temperature readings from the sensors 120–124. The software uses these four parameters to correlate temperature readings with an estimated location of each individual vertebra.

In the preferred embodiment, currently available normative data indicates that within a given spinal region, the vertebra are evenly distributed. Marking the transitions between each spinal region results in knowing the length of each region for the patient, i.e., the distance traveled along each region by the hand held scanner. Dividing the length of a given patient's spinal regions by the number of vertebra in each spinal region results in a figure which estimates the spacing between each vertebra in that region. Once the estimated location of each vertebra is calculated in that manner, the location can be correlated to the distance traveled by the scanner to reach that location. Then, the temperature measured at that location can be associated with the vertebra at that location.

After correlating the temperature readings to the estimated location of the individual vertebra, the software also generates graphical displays of the temperature measured on the left and the right sides of each vertebra.

Figure 5:
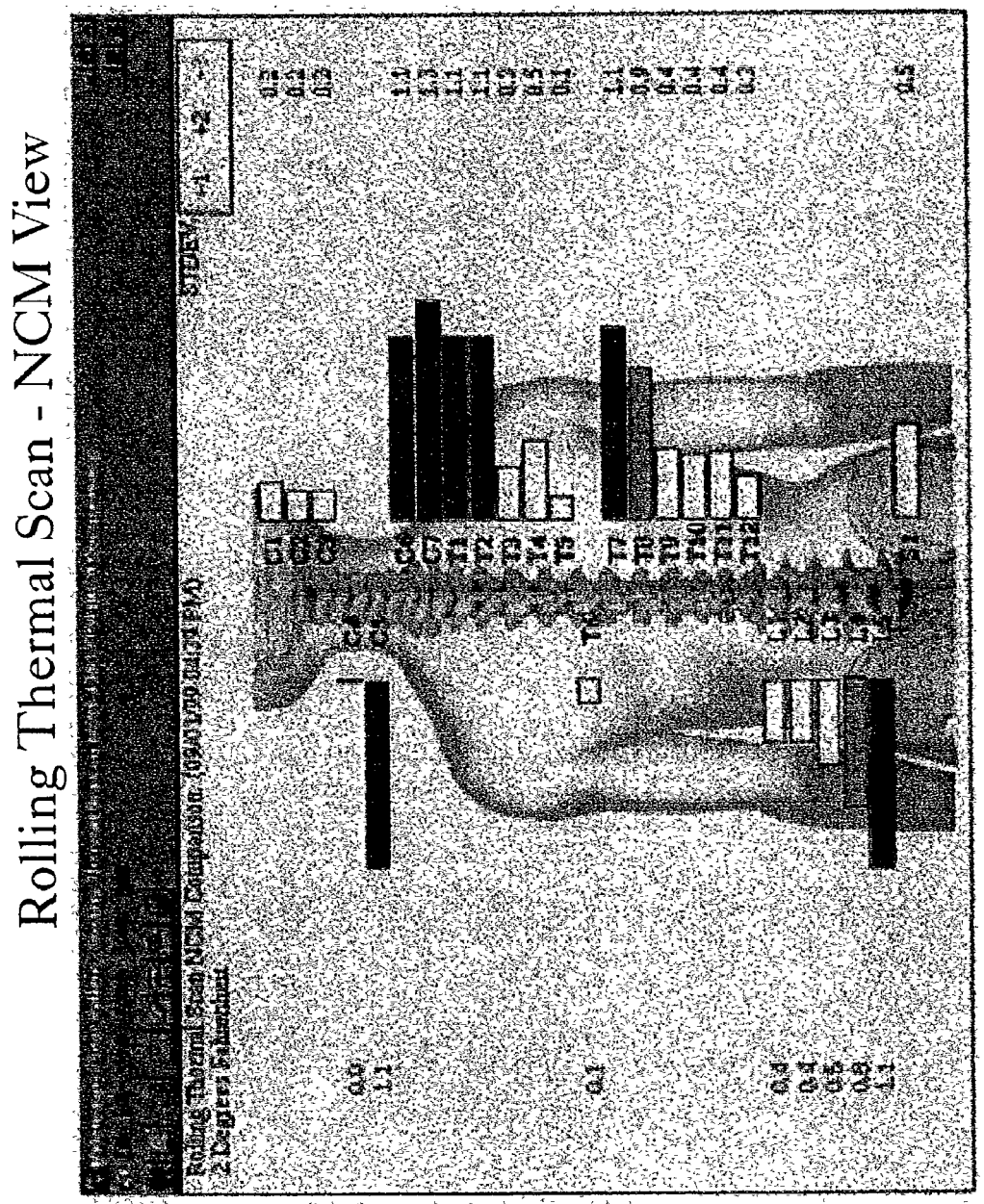
FIG. 5 illustrates one embodiment of a graphical display for a rolling thermal scan.

FIG. 5 illustrates one embodiment of a graphical display for a rolling thermal scan. In one embodiment, the software displays the absolute temperature readings as horizontal bars on a left and a right side of each vertebra. The user can visually compare any temperature difference between the left and the right side of each vertebra. The software gives the user an option to choose a specific temperature range or use an autoscale feature which selects a scale to include the highest scanned value. The software also gives the user an option to display a muscle view or a spine view. In another embodiment, the software displays the difference between temperature readings on the left side and temperature readings on the right side.

Figure 6:
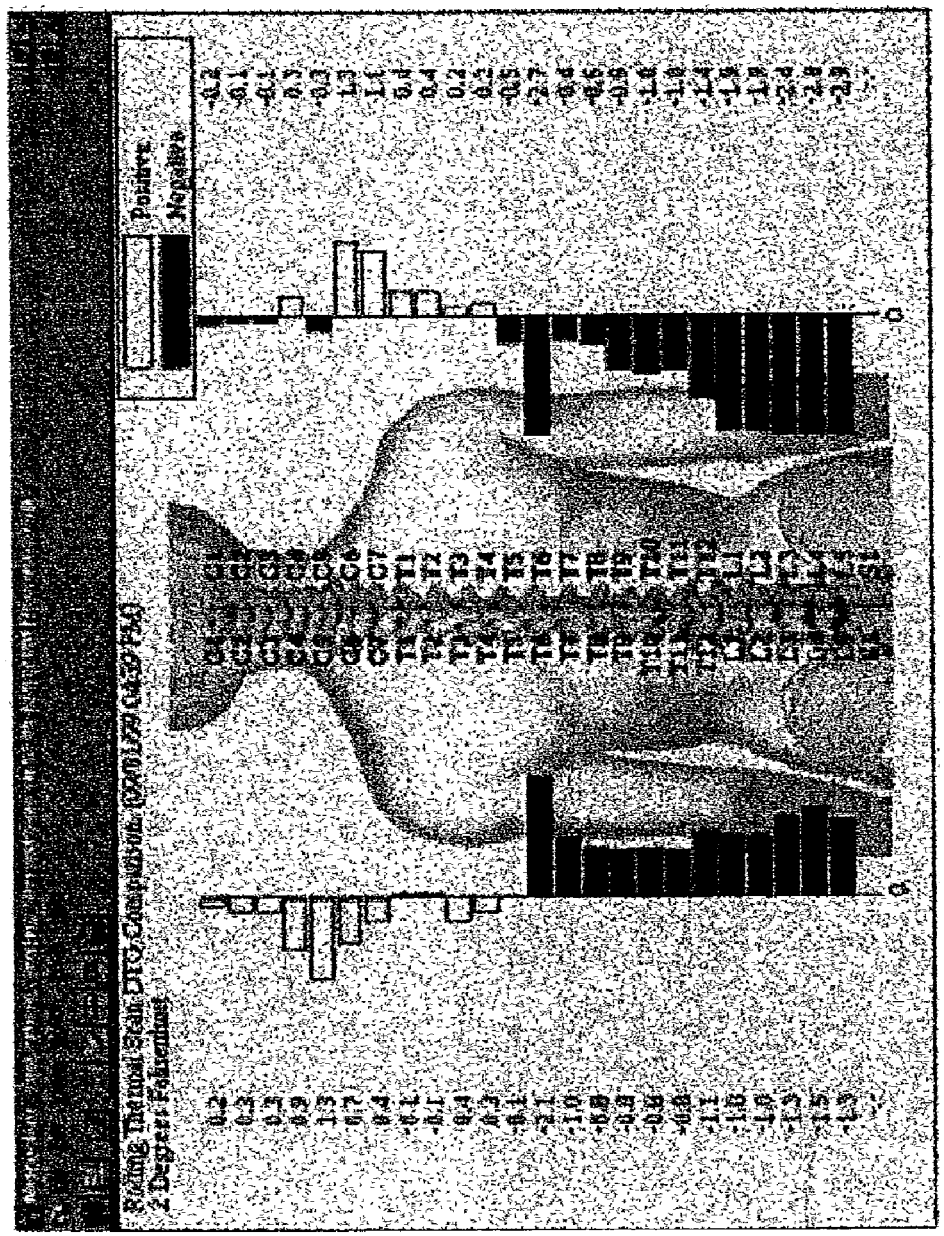
FIG. 6 illustrates another embodiment of a graphical display for a rolling thermal scan.

FIG. 6 illustrates another embodiment of a graphical display for a rolling thermal scan. In FIG. 6, the software compares each temperature reading on a left and a right side of each vertebra to the temperature reading taken at S-1 and displays the values as horizontal bars. The software also gives the user an option to compare the temperature readings to normative data stored in a database in the computer's memory or on a disk.

Figure 7:
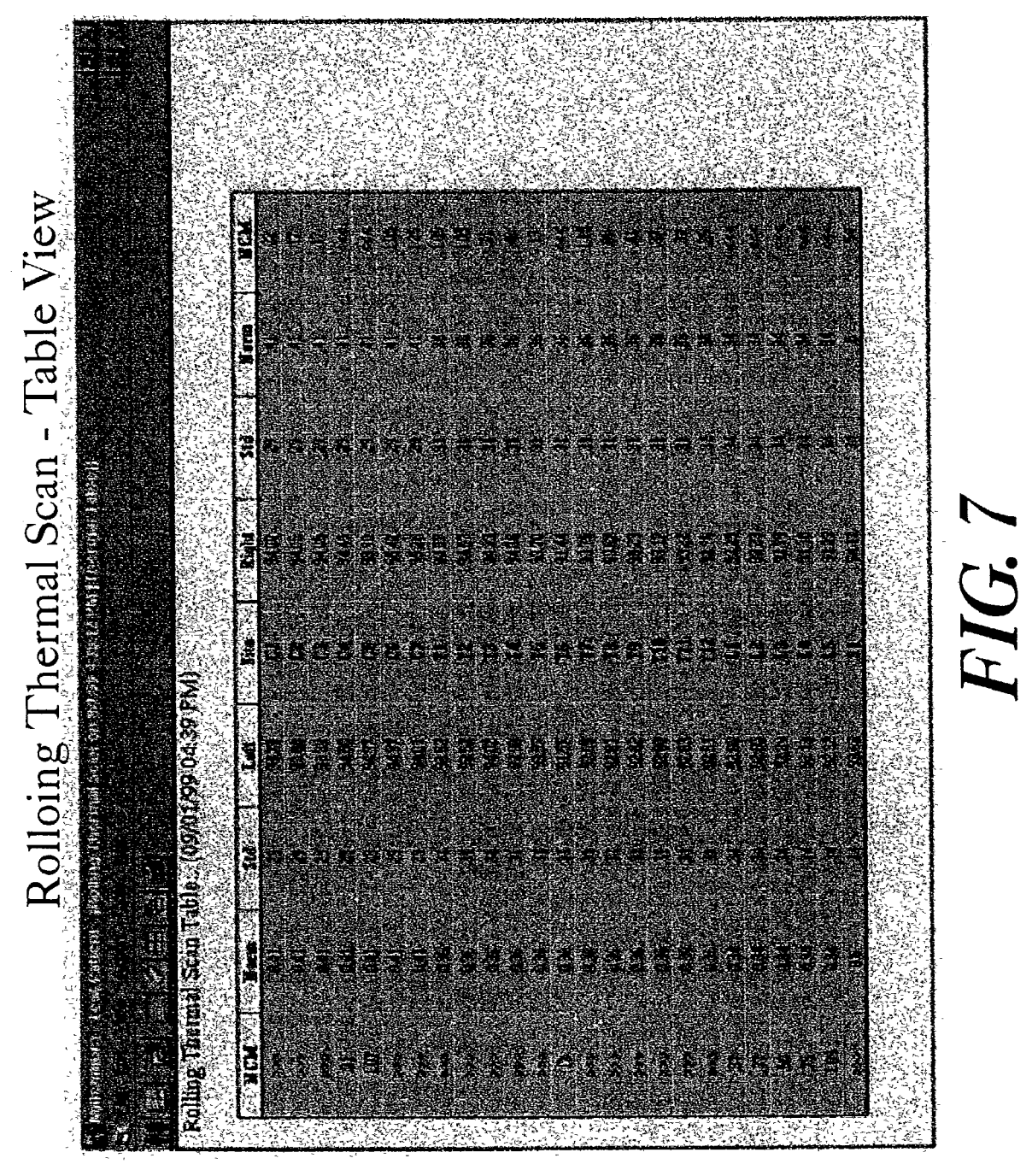
Figure 8:
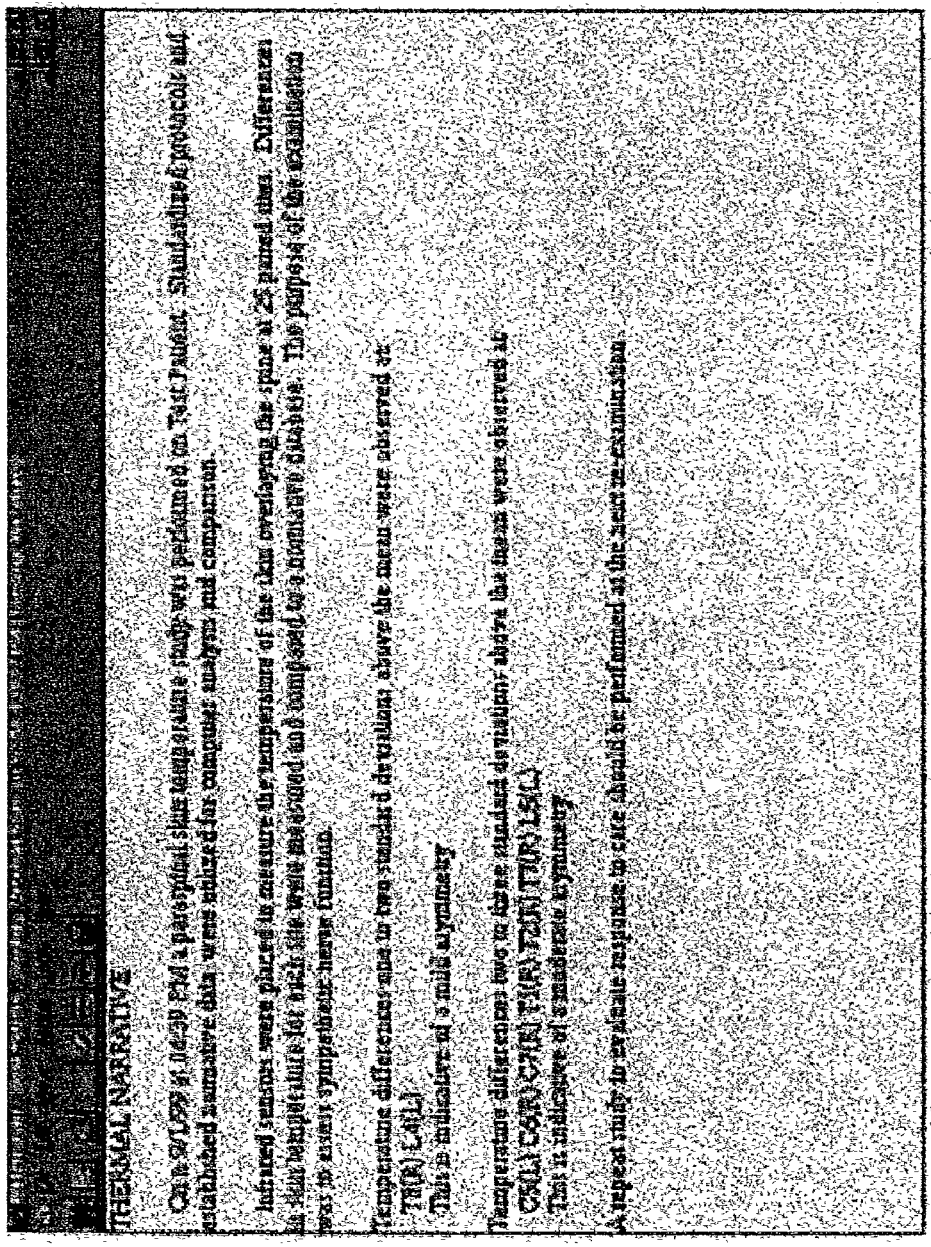
FIG. 8 illustrates one embodiment of a narrative display for a rolling thermal scan.
Figure 9:
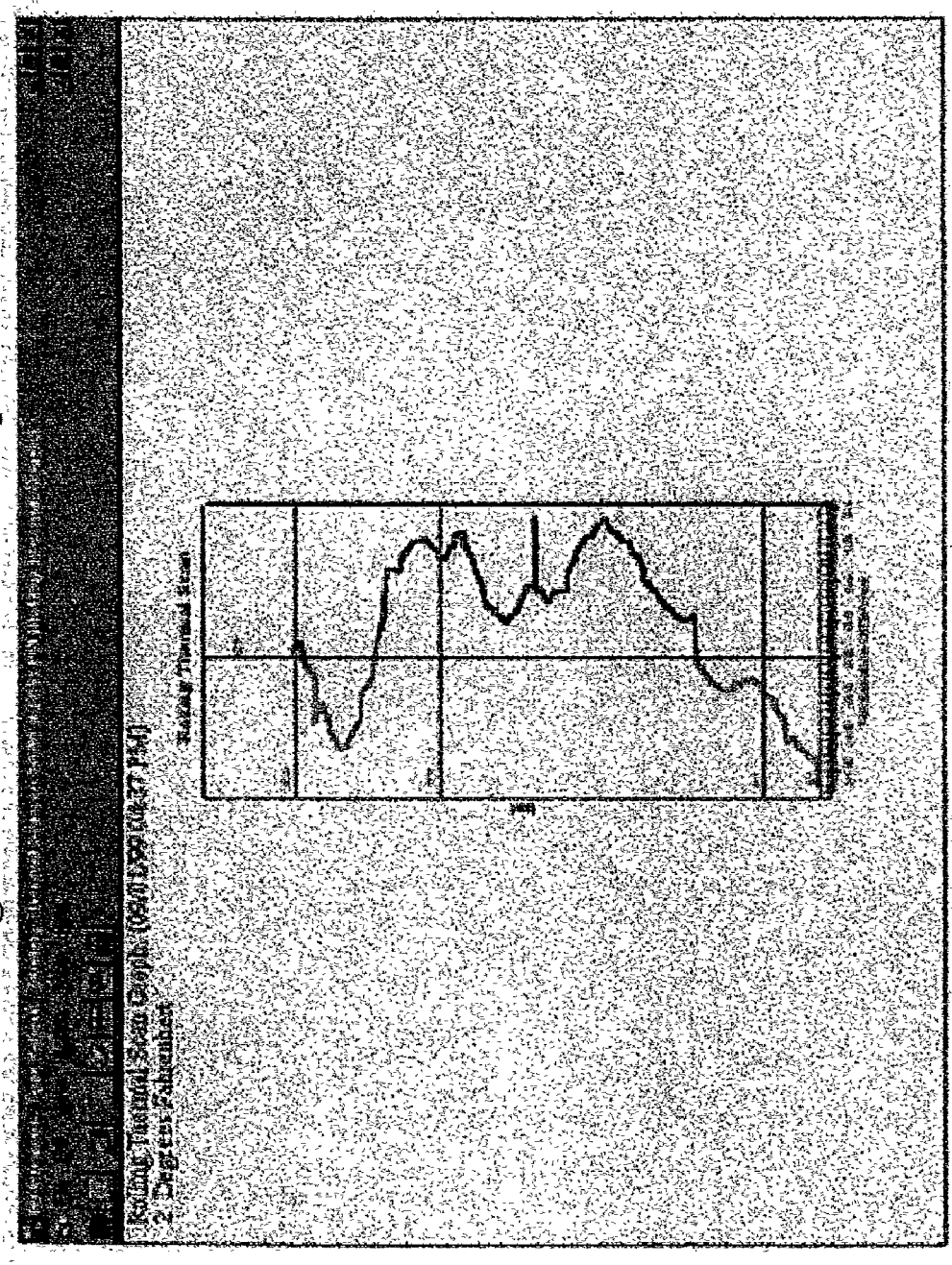
FIG. 9 illustrates one embodiment of a real-time graphical display for a rolling thermal scan.

FIG. 7 illustrates one embodiment of a table display for a rolling thermal scan by the device 100. FIG. 8 illustrates one embodiment of a narrative display for a rolling thermal scan. In FIG. 8, the software analyzes the temperature readings and their standard deviation and provides a text analysis. For example, the software may point out problem areas near particular areas of the spine. FIG. 9 illustrates one embodiment of a real-time graphical display for a rolling thermal scan by the device 100. The software may display an instantaneous bilateral differential temperature difference (in degrees per inch).

Figure 10:
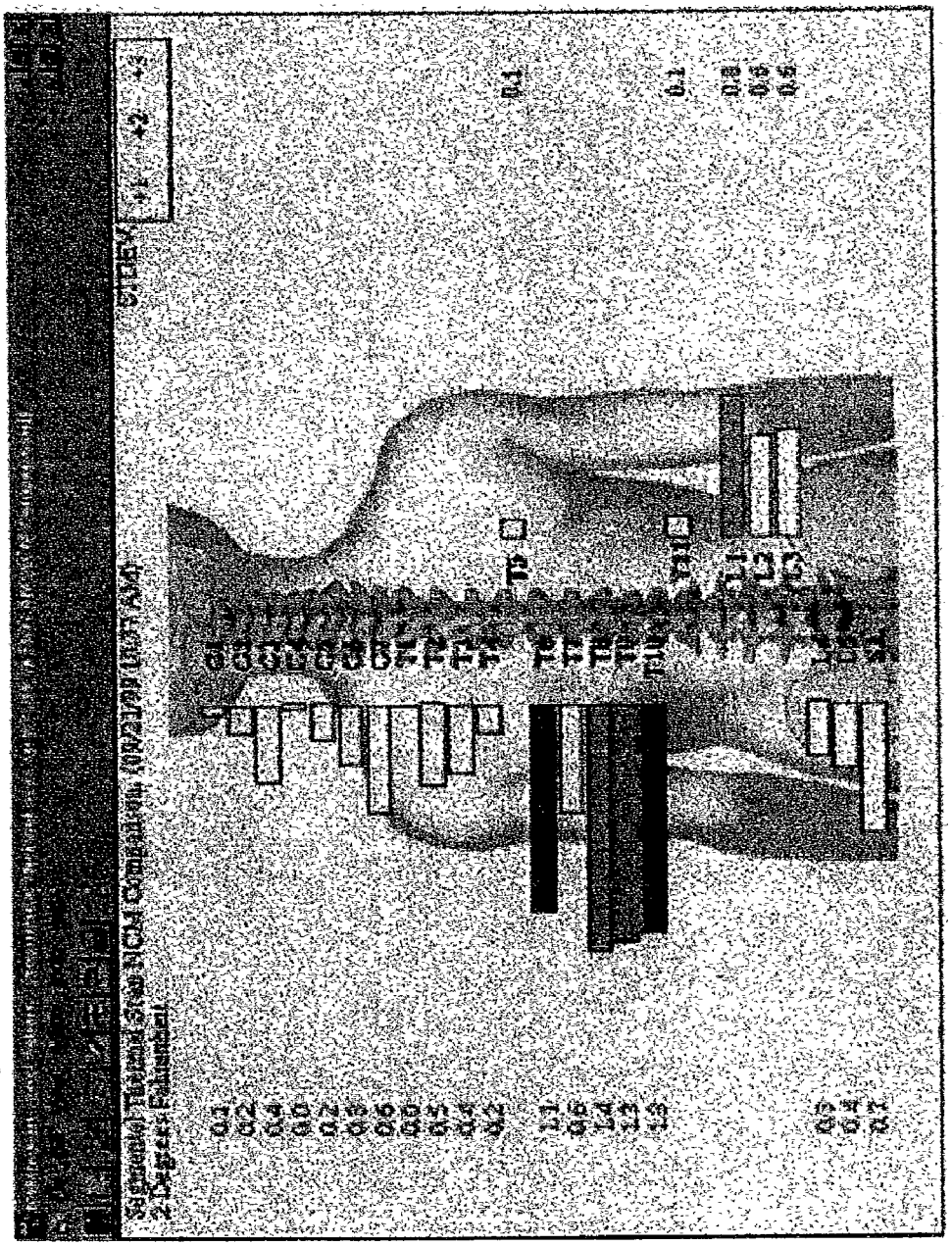
FIG. 10 illustrates one embodiment of a graphical display for a segmental thermal scan.
Figure 11:
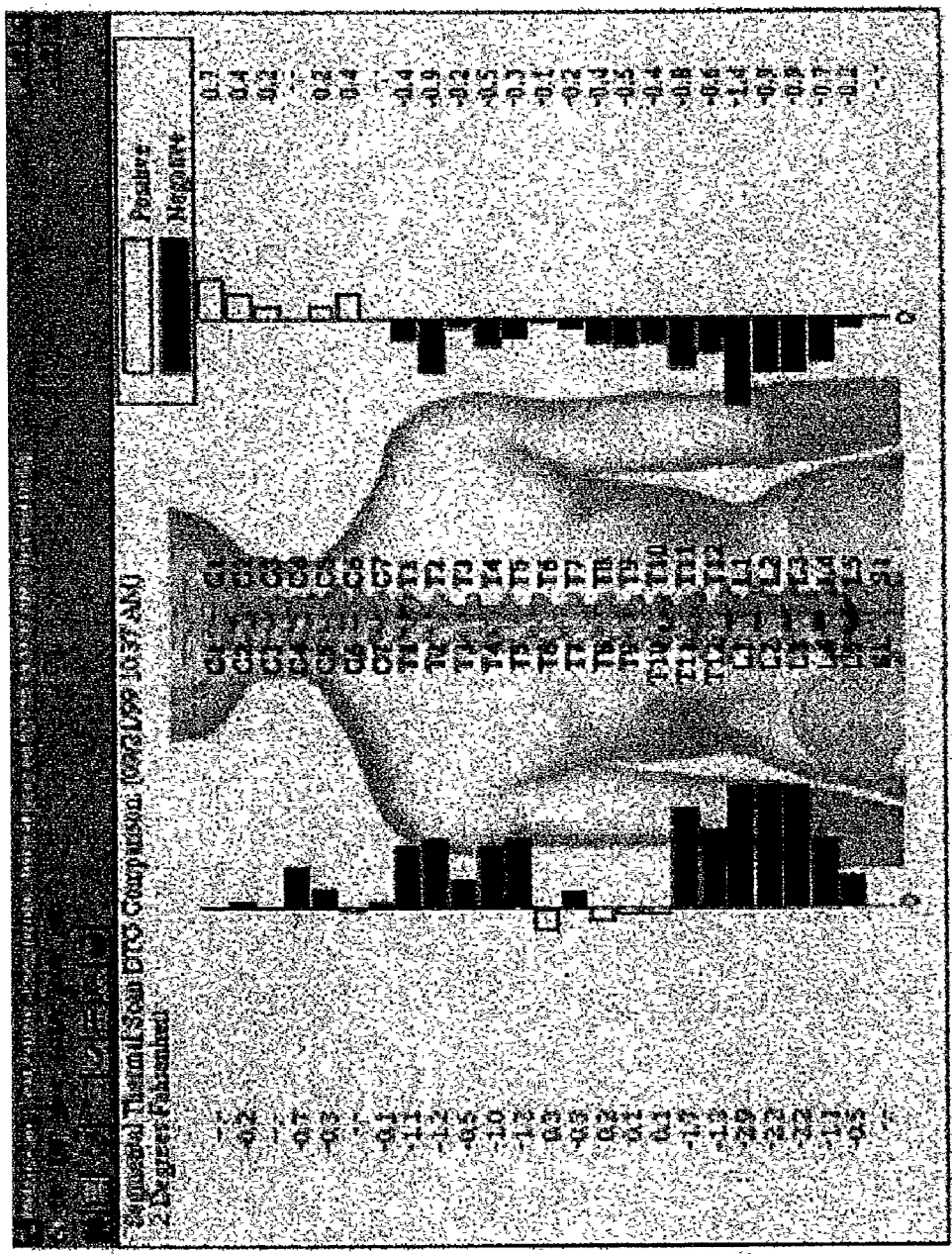
FIG. 11 illustrates another embodiment of a graphical display for a segmental thermal scan.
Figure 12:
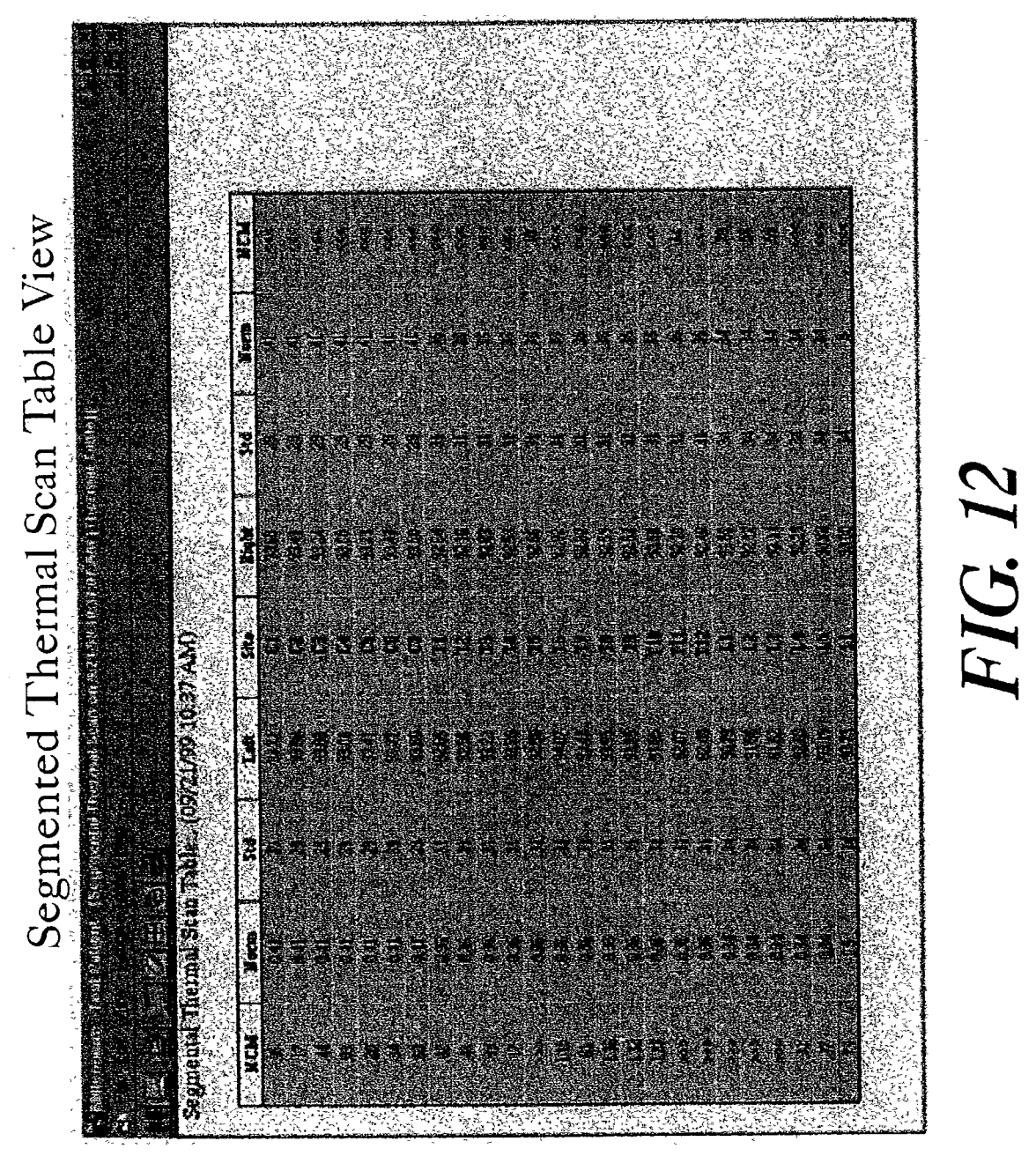
Figure 13:
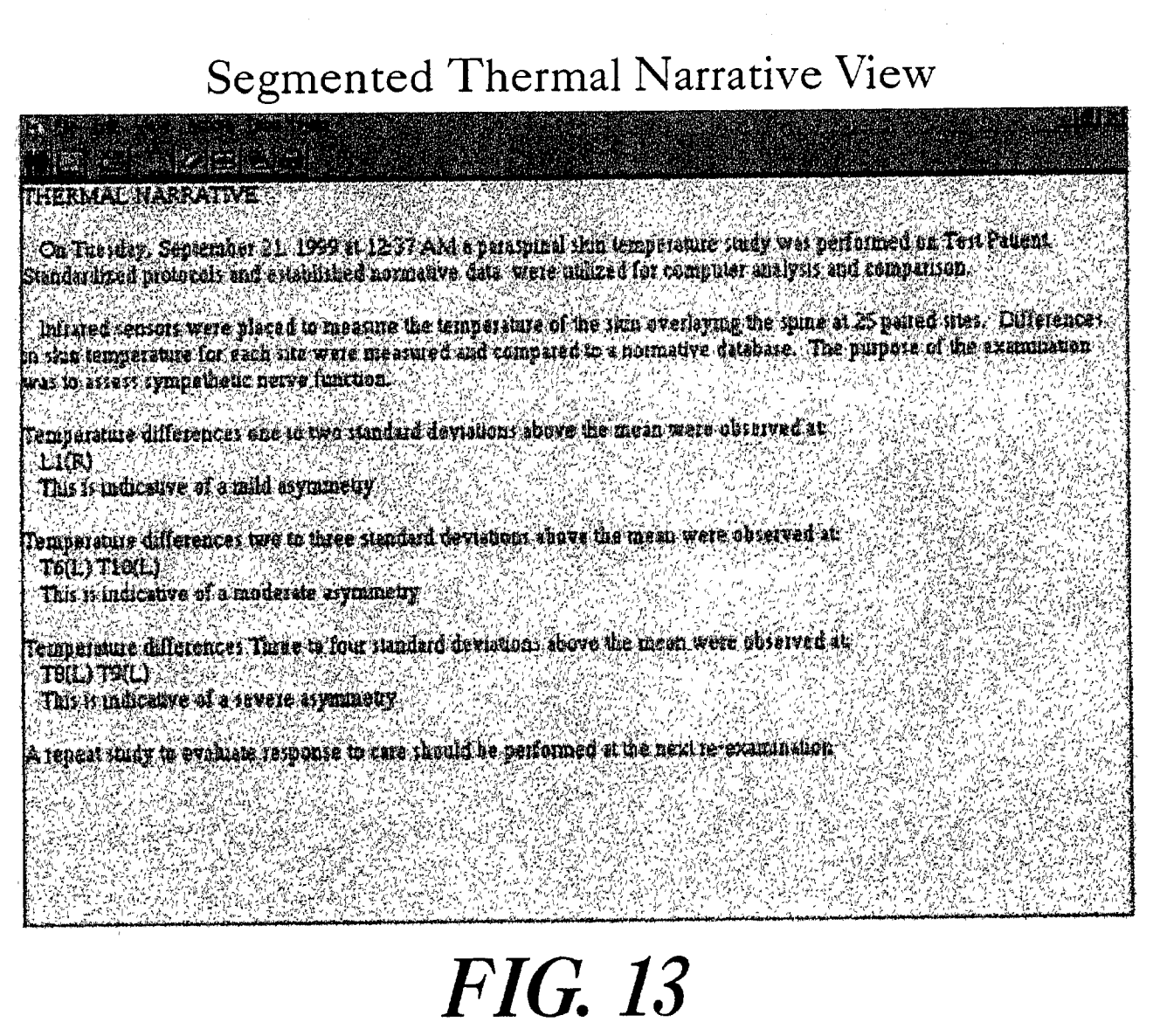

In one embodiment, the software displays graphical displays for segmental thermal scanning that are substantially similar to the graphical displays for rolling thermal scanning. FIG. 10 illustrates one embodiment of a graphical display for a segmental thermal scan. FIG. 11 illustrates another embodiment of a graphical display for a segmental thermal scan. FIG. 12 illustrates one embodiment of a table display for a segmental thermal scan. FIG. 13 illustrates one embodiment of a narrative display for a segmental thermal scan.

Preferably, a user can simultaneously view multiple temperature readings from two or more graphical displays. The software may allow the user to select between (1) viewing two graphical displays side-by-side or (2) superimposing one set of temperature readings onto another set of temperature readings. For example, the software may display side-by-side or superimpose two sets of temperature readings from two different days or from two different patients. Thus, the software allows the user to compare and analyze different scan types for a patient, different scans from different days and/or different aspects of the same scan. The software also allows the user to print any of the aforementioned displays.

In one embodiment, the software allows the user to decide whether or not to save a particular scan result or graphical display. The software may store files related to a plurality of patients. The software allows the user to update or delete existing patient files and add new patient files to the database. Each patient file comprises identification information, e.g. name, age, etc., and measured thermal data.

Synchronization

From time to time, the sensors 120–124 may produce skewed or 'one-sided' temperature readings due to changes in the sensors' original factory settings. To synchronize the sensors 120–124, the user uses a reference point for synchronizing all three sensors 120–124, preferably on a warmer part of the body. The software prompts the user to place the first sensor 120, the second sensor 122 and the third sensor 124 sequentially on the reference point. The software will inform the user whether which sensors 120–124 need to be synchronized, if any. If one or more sensors 120–124 need to be synchronized, an offset value may be added or subtracted to one or more sensors 120–124. In one embodiment, the sensors 120–124 may be calibrated by adding an offset value to two of the lower reading sensors to bring them to substantially the same level as the highest reading sensor.

The invention may be embodied in other specific forms without departing from its spirit or essential characteristics. The described embodiment is to be considered in all respects only as illustrative and not restrictive and the scope of the invention is, therefore, indicated by the appended claims rather than the foregoing description. All changes which come within the meaning and range of equivalency of the claims are to be embraced within their scope.

What is claimed is:

1. A thermal scanning system adapted to scan skin temperature on opposite sides of a patient's spinal column for patients of different sizes, the thermal scanning system comprising:
   a handheld body having a portion which is adapted to be gripped by a user at least when scanning;
   a plurality of temperature sensors oriented in a fixed position relative to said body, including a first sensor, a second sensor and a third sensor, wherein the sensors are mounted on the body and arranged in a linear fashion such that the first and second sensors are spaced to scan skin temperature on opposite sides of a patient's spinal column of a first size range, the second and third sensors are spaced to scan skin temperature on opposite sides of a patient's spinal column of a second size range, and the first and third sensors are spaced to scan skin temperature on opposite sides of a patient's spinal column of a third size range, wherein the size range defined between any two of the three temperature sensors is different from the size range between any other combination of two sensors, each sensor producing a data signal indicative of sensed temperatures;
   a computer receiving and processing the data signals received from two or more of the sensors; and
   a selector defining at least first, second and third operational modes for the thermal scanning system, wherein the computer in the first operational mode uses the data signals received from the first and second sensors to determine the skin temperature on opposite sides of a patient's spinal column, wherein the computer in the second operational mode uses the data signals received from the first and third sensors to determine the skin temperature on opposite sides of a patient's spinal column, and wherein the computer in the third operational mode uses the data signals received from the second and third sensors to determine the skin temperature on opposite sides of a patient's spinal column.

2. The system of claim 1, wherein the first size range relates to an infant, the second size range relates to a child and the third size range relates to an adult.

3. The system of claim 1, wherein the sensors scan at least a first point and a second point, the points being located on opposite sides of a patient's spinal column or vertebra selected by the user.

4. The system of claim 1, wherein the sensors scan a plurality of points on opposite sides of the patient's spinal column.

5. The system of claim 1, further comprising a display device, the display device displaying a first temperature reading from a point located on a left side of a patient's vertebra and a second temperature reading from a point located on a right side of the patient's vertebra.

6. The system of claim 1, further comprising a display device, the display device displaying a first comparison value and a second comparison value, the first comparison value comprising a first temperature reading from a point located on a left side of a patient's vertebra adjusted by a reference value, the second comparison value comprising a second temperature reading from a point located on a right side of the patient's vertebra adjusted by the reference value.

7. The system of claim 1, further comprising a display device, the display device displaying a difference between a first temperature reading from a point located on one side of a patient's vertebra and a second temperature reading from a point located on the other side of the patient's vertebra.

8. The system of claim 1 wherein the sensors are aligned in a linear fashion, with the first sensor on one end, the third sensor on another end and the second sensor positioned between the first and third sensors, the second sensor closer to the first sensor than to the third sensor.

9. A thermal scanning system adapted to scan skin temperature on opposite sides of a patient's spinal column for patients of different sizes, the thermal scanning system comprising:
   a handheld body having at least a portion which is adapted to be gripped by a user at least when scanning;
   a plurality of temperature sensors oriented in a fixed position relative to said body, including a first sensor, a second sensor and a third sensor, wherein the sensors are mounted on the body and arranged in a linear fashion such that the first and second sensors are spaced to scan skin temperature on opposite sides of a patient's spinal column of a first size range, the second and third sensors are spaced to scan skin temperature on opposite sides of a patient's spinal column of a second size range, and the first and third sensors are spaced to scan skin temperature on opposite sides of a patient's spinal column of a third size range, wherein the size range defined between any two of the three temperature sensors is different from the size range between any other combination of two sensors;
   wherein the system obtains a signal from said first sensor indicative of a first temperature reading;
   wherein the system obtains a signal from said second sensor indicative of a second temperature reading;
   wherein the system obtains a signal from said third sensor indicative of a third temperature reading;
   wherein the first, second, and third temperature readings are independent of each other;
   a computer receiving and processing the temperature readings received from two or more of the sensors, the computer using only two of the three temperature readings from the first, second and third sensors to determine the skin temperature on opposite sides of a patient's spinal column; and
   a selector cooperating with the computer to establish which two of the three temperature readings the computer uses to determine the skin temperature on opposite sides of a patient's spinal column.

10. The system of claim 9, wherein the first size range relates to an infant, the second size range relates to a child and the third size range relates to an adult.

11. The system of claim 9, wherein the sensors scan at least a first point and a second point, the points being located on opposite sides of a patient's spinal column or vertebra selected by the user.

12. The system of claim 9, wherein the sensors scan a plurality of points on opposite sides of the patient's spinal column.

13. The system of claim 9, further comprising a display device, the display device displaying a first temperature reading from a point located on a left side of a patient's vertebra and a second temperature reading from a point located on a right side of the patient's vertebra.

14. The system of claim 9, further comprising a display device, the display device displaying a first comparison value and a second comparison value, the first comparison value comprising a first temperature reading from a point located on a left side of a patient's vertebra adjusted by a reference value, the second comparison value comprising a second temperature reading from a point located on a right side of the patient's vertebra adjusted by the reference value.

15. The system of claim 9, further comprising a display device, the display device displaying a difference between a first temperature reading from a point located on one side of a patient's vertebra and a second temperature reading from a point located on the other side of the patient's vertebra.

16. The system of claim 9, wherein the sensors are aligned in a linear fashion, with the first sensor on one end, the third sensor on another end and the second sensor positioned between the first and third sensors, the second sensor closer to the first sensor than to the third sensor.

17. A thermal scanning system adapted to scan skin temperature on opposite sides of a patient's spinal column for patients of different sizes, the thermal scanning system comprising:
   a handheld body having at least a portion which is adapted to be gripped by a user at least when scanning;
   a plurality of temperature sensors oriented in a fixed position relative to said body, including a first sensor, a second sensor and a third sensor, wherein the sensors are mounted on the body and arranged in a linear fashion such that the first and second sensors are spaced to scan skin temperature on opposite sides of a patient's spinal column of a first size range, the second and third sensors are spaced to scan skin temperature on opposite sides of a patient's spinal column of a second size range, and the first and third sensors are spaced to scan skin temperature on opposite sides of a patient's spinal column of a third size range, wherein the size range defined between any two of the three temperature sensors is different from the size range between any other combination of two sensors, wherein the sensors scan a first point and a second point, the points being located on opposite sides of the patient's spinal column or vertebra selected by the user, each sensor producing a data signal indicative of sensed temperatures;
   a computer receiving and processing the data signals received from two or more of the sensors; and
   a selector defining a plurality of operational modes for the thermal scanning system, wherein the computer in at least one of the operational modes does not use the data signal from the first sensor to determine the skin temperature on opposite sides of a patient's spinal column, and in at least another one of the operational modes does not use the data signal from the second sensor to determine the skin temperature on opposite sides of a patient's spinal column.

* * * * *

UNITED STATES PATENT AND TRADEMARK OFFICE
CERTIFICATE OF CORRECTION

| | | |
|---|---|---|
| PATENT NO. | : 7,115,098 B2 | Page 1 of 1 |
| APPLICATION NO. | : 10/173336 | |
| DATED | : October 3, 2006 | |
| INVENTOR(S) | : Patrick Gentempo and Lee Brody | |

It is certified that error appears in the above-identified patent and that said Letters Patent is hereby corrected as shown below:

Title page, item [54] title, please delete "ADJUSTABLE" and insert -- ADAPTABLE--, therefore.

Column 1, line 1, please delete "ADJUSTABLE" and insert -- ADAPTABLE --, therefore.

Column 1, line 7, after "2000" please insert -- , --.

Column 4, line 44, please delete "143" and insert -- 134. --, therefore.

Signed and Sealed this

Twenty-fourth Day of July, 2007

JON W. DUDAS
*Director of the United States Patent and Trademark Office*